(12) United States Patent
Mayoux et al.

(10) Patent No.: US 12,427,161 B2
(45) Date of Patent: Sep. 30, 2025

(54) METHODS FOR TREATING AND PHARMACEUTICAL COMPOSITIONS

(71) Applicant: Boehringer Ingelheim International GmbH, Ingelheim am Rhein (DE)

(72) Inventors: Eric Williams Mayoux, Gambais (FR); Delphine Behr-Roussel, Viroflay (FR); Francois Giuliano, Paris (FR)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 18/506,169

(22) Filed: Nov. 10, 2023

(65) Prior Publication Data

US 2024/0082284 A1    Mar. 14, 2024

Related U.S. Application Data

(63) Continuation of application No. 17/494,543, filed on Oct. 5, 2021, now abandoned, which is a continuation of application No. 16/446,109, filed on Jun. 19, 2019, now abandoned, which is a continuation of application No. 15/568,602, filed as application No. PCT/EP2016/059525 on Apr. 28, 2016, now abandoned.

(30) Foreign Application Priority Data

Apr. 30, 2015   (EP) .................................... 15166057

(51) Int. Cl.
| | |
|---|---|
| *A61K 31/7048* | (2006.01) |
| *A61K 31/5575* | (2006.01) |
| *A61K 45/06* | (2006.01) |
| *A61P 3/10* | (2006.01) |
| *A61P 15/10* | (2006.01) |

(52) U.S. Cl.
CPC ...... *A61K 31/7048* (2013.01); *A61K 31/5575* (2013.01); *A61K 45/06* (2013.01); *A61P 3/10* (2018.01); *A61P 15/10* (2018.01); *A61K 2300/00* (2013.01)

(58) Field of Classification Search
CPC ............ A61K 31/7048; A61K 31/5575; A61K 45/06; A61K 2300/00; A61P 15/10; A61P 3/10
USPC .......................................................... 514/23
See application file for complete search history.

(56) References Cited

U.S. PATENT DOCUMENTS

| | | | |
|---|---|---|---|
| 11,666,590 B2* | 6/2023 | Broedl ................. | A61K 31/522 514/23 |
| 2013/0252908 A1* | 9/2013 | Mayoux ............. | A61K 31/7048 514/23 |
| 2014/0315832 A1* | 10/2014 | Broedl ................... | A61P 43/00 514/23 |

FOREIGN PATENT DOCUMENTS

| | | |
|---|---|---|
| CA | 2557801 A1 | 10/2005 |
| WO | 2005092877 A1 | 10/2005 |

OTHER PUBLICATIONS

Glossary of medical education terms, Institute of International Medical Education. http://www.iime.org/glossary.htm Accessed in Apr. 20, 2024. (Year: 2024).*

(Continued)

*Primary Examiner* — Yih-Horng Shiao
(74) *Attorney, Agent, or Firm* — David L. Kershner (57) ABSTRACT

The invention relates to methods for improving glycemic control and for treating erectile dysfunction in a patient diagnosed with prediabetes, type 1 diabetes mellitus, type 2 diabetes mellitus or metabolic syndrome wherein a sodium glucose co-transporter 2 (SGLT2) inhibitor is administered to the patient. Furthermore the invention relates to a method for improving a treatment of erectile dysfunction in a male patient diagnosed with prediabetes, type 1 diabetes mellitus or type 2 diabetes mellitus characterized in that in addition to the treatment of erectile dysfunction a SGLT2 inhibitor is administered to the patient. The invention also relates a pharmaceutical composition comprising a SGLT2 inhibitor and a compounds selected from the group consisting of phosphodiesterase 5 (PDE5) inhibitors or alprostadil.

3 Claims, 4 Drawing Sheets

(56) References Cited

OTHER PUBLICATIONS

Takakura et al. Effect of ipragliflozin, an SGLT2 inhibitor, on progression of diabetic microvascular complications in spontaneously diabetic Torii fatty rats. Life Sciences 147 (2016) 125-131. (Year: 2016).*
Kohan et al. Interleukin 1 modulation of renal epithelial glucose and amino acid transport. Am. J. Physiol. 254 (Renal Fluid Electrolyte Physiol. 23): F879-F886, 1988. (Year: 1988).*
Wagman et al. Current Therapies and Emerging Targets for the Treatment of Diabetes. Current Pharmaceutical Design, 2001, 7, 417-450. (Year: 2001).*
Romeo et al. Sexual Function in Men With Diabetes Type 2: Association With Glycemic Control. Journal of Urology, vol. 163, 788-791, Mar. 2000. (Year: 2000).*
Basu et al. New Treatment Options for Erectile Dysfunction in Patients with Diabetes Mellitus. Drugs 2004; 64 (23): 2667-2688. (Year: 2004).*
Ho, Chen-Hsun et al. "The Prevalence and the Risk Factors of Testosterone Deficiency in Newly Diagnosed and Previously Known Type 2 Diabetic Men" (2015) International Society for Sexual Medicine, 12, 389-397.
Hussar, Daniel A. et al. "2015 New Drug Update" The Consultant Pharmacist, (2015) vol. 30, No. 4, 192-208.
Assaly, Rana et al. "Added Benefit of Empagliflozin: Improvement of Erectile Dysfunction in Diabetic Type 2 Rats" (2015) XP-002758690, AN: PREV201500747898; 2 pgs.
Weinberg, Aviva E. et al. "Diabetes Severity, Metabolic Syndrome and the Risk of Erectile Dysfunction" (2013) International Society for Sexual Medicine 10:3, 3102-3109.
International Search Report for PCT/EP2016/059525 mailed Apr. 28, 2016.

* cited by examiner

METHODS FOR TREATING AND PHARMACEUTICAL COMPOSITIONS

TECHNICAL FIELD OF THE INVENTION

The invention relates to a method for improving glycemic control in a male patient diagnosed with prediabetes, type 1 diabetes mellitus, type 2 diabetes mellitus or metabolic syndrome and with erectile dysfunction. Furthermore the invention relates to a method for treating erectile dysfunction in a male patient diagnosed with prediabetes, type 1 diabetes mellitus, type 2 diabetes mellitus or metabolic syndrome. In addition the invention relates to a method for improving a treatment of erectile dysfunction in a male patient diagnosed with prediabetes, type 1 diabetes mellitus, type 2 diabetes mellitus or metabolic syndrome. Furthermore the invention relates to a pharmaceutical composition comprising a SGLT2 inhibitor and one or more compounds selected from the group consisting of PDE5 inhibitors or alprostadil.

BACKGROUND OF THE INVENTION

The rising prevalences of obesity and type 2 diabetes mellitus (T2DM) represent major challenges for global public health. Worldwide, there are more than 220 million adults with type 2 diabetes mellitus, figures which are projected to rise to 366 million by 2030 (World Health Organisation 2010; International Diabetes Federation 2010). According to the US Centers for Disease Control and Prevention, rates of type 2 diabetes mellitus have tripled in the past 30 years. Diabetes now affects an estimated 23.6 million people in the United States; another 57 million have prediabetes. Prediabetes raises short-term absolute risk of type 2 diabetes mellitus five- to sixfold.

Type 2 diabetes mellitus is an increasingly prevalent disease that due to a high frequency of complications leads to a significant reduction of life expectancy. Because of diabetes-associated microvascular complications, type 2 diabetes is currently the most frequent cause of adult-onset loss of vision, renal failure, and amputations in the industrialized world. In addition, the presence of type 2 diabetes mellitus is associated with a two to five fold increase in cardiovascular disease risk.

After long duration of disease, most patients with type 2 diabetes mellitus will eventually fail on oral therapy and become insulin dependent with the necessity for daily injections and multiple daily glucose measurements.

Oral antidiabetic drugs conventionally used in therapy (such as e.g. first- or second-line, and/or mono- or (initial or add-on) combination therapy) include, without being restricted thereto, metformin, sulphonylureas, thiazolidinediones, DPPIV inhibitors, SGLT2 inhibitors, glinides, α-glucosidase inhibitors.

Erectile dysfunction is defined as the persistent inability to attain or maintain a penile erection sufficient for satisfactory sexual performance. Therefore erectile dysfunction has a significant impact on the physical and psychosocial health aspects of men and their partners. The prevalence of this condition increases with age. In a large cross-sectional, community-based study, 2 among men between the ages of 40 and 49 years, the prevalence of complete or severe erectile dysfunction was 5%, while among men between the ages of 70 and 79 years, these rates were 15% and 34%, respectively. Erectile dysfunction affects about 30 million men in USA and it has been estimated that the worldwide prevalence of erectile dysfunction will be 322 million cases by the year 2025.

Erectile dysfunction (ED) is even more common in diabetic populations. Studies of ED suggest that its prevalence in men with diabetes ranges from 35-75% versus 26% in general population. Moreover the onset of ED also occurs 10-15 years earlier in men with diabetes than it does in sex-matched counterparts without diabetes. Moreover, for patients with diabetes, the risk of erectile dysfunction increase with the duration of the condition and with increasing levels of glycated hemoglobin. Erectile dysfunction can also be linked to other conditions common in men with diabetes, such as high blood pressure and coronary artery disease and metabolic syndrome. Coexistence of hypertension, CVD and poor glycemic control worsens ED.

PDE5 inhibitors on demand or daily dosing (such as tadalafil) are the recommended first-line treatment for ED. However, their use is not recommended in men who have recent history of stroke or myocardial infarction (within the last 6-8 weeks), or who have significantly low blood pressure, uncontrolled high blood pressure, unstable angina, severe cardiac failure, severe liver impairment or end-stage kidney disease requiring dialysis. Furthermore diabetic men have displayed impaired response rates in therapeutic trials with PDE5 inhibitors (Kendirci M, Tanriverdi O, Trost L, Hellstrom W J. Management of sildenafil treatment failures. Curr Opin Urol 2006; 16:449-459). In case of failure of PDE5 inhibitors in diabetic patients complaining about erectile dysfunction, on demand intracavernosal injections of prostagandin E1 or alprostadil are recommended. Limitations of intracavernosal injections of prostagandin E1 or alprostadil in diabetic patients are their invasivesness and possible pain.

In view of the limitation of the existing therapies there is still an unmet medical need to treat erectile dysfunction, in particular in patients with diabetes mellitus.

Empagliflozin is a novel SGLT2 inhibitor that is described for the treatment or improvement in glycemic control in patients with type 2 diabetes mellitus, for example in WO 05/092877, WO 06/117359, WO 06/120208, WO 2010/092126, WO 2010/092123, WO 2011/039107, WO 2011/039108, WO 2014/161918, WO 2014/161919 and WO 2014/170383.

AIM OF THE PRESENT INVENTION

An aim of the present invention is to provide a method for improving glycemic control in a patient diagnosed with prediabetes, type 1 diabetes mellitus, type 2 diabetes mellitus or metabolic syndrome in a male patient diagnosed with erectile dysfunction.

Another aim of the present invention is to provide a method for treating erectile dysfunction in a male patient diagnosed with prediabetes, type 1 diabetes mellitus, type 2 diabetes mellitus or metabolic syndrome.

Yet another aim of the present invention is to provide a pharmaceutical composition, in particular for improving glycemic control in a patient diagnosed with prediabetes, type 1 diabetes mellitus, type 2 diabetes mellitus or metabolic syndrome and for treating erectile dysfunction.

Further aims of the present invention become apparent to the one skilled in the art by description hereinbefore and in the following and by the examples.

SUMMARY OF THE INVENTION

Within the scope of the present invention it has now been found that an administration of a SGLT2 inhibitor improved the erectile responses in diabetic animals. Beside its effect in improving glycemic control the SGLT2 inhibitor has further advantageous properties of clinical relevance, such as the insulin independent mechanism, a weight-reducing effect and a lowering effect on the blood-pressure. Therefore the observed pro-erectile effect of an administration of the SGLT2 inhibitor could become a highly valuable treatment option for diabetic patients suffering from erectile dysfunction.

Therefore, in a first aspect the present invention provides a method for improving glycemic control in a patient diagnosed with prediabetes, type 1 diabetes mellitus, type 2 diabetes mellitus or metabolic syndrome wherein a SGLT2 inhibitor is administered to the patient characterized in that the patient is a male patient diagnosed with erectile dysfunction.

According to another aspect the present invention provides a method for treating erectile dysfunction in a male patient diagnosed with prediabetes, type 1 diabetes mellitus, type 2 diabetes mellitus or metabolic syndrome characterized in that a SGLT2 inhibitor is administered to the patient.

The observed pro-erectile effect of an administration of a SGLT2 inhibitor may support or improve a treatment of erectile dysfunction in a patient.

Therefore according to another aspect the present invention provides a method for improving a treatment of erectile dysfunction in a male patient diagnosed with prediabetes, type 1 diabetes mellitus, type 2 diabetes mellitus or metabolic syndrome characterized in that in addition to the treatment of erectile dysfunction a SGLT2 inhibitor is administered to the patient.

Known treatments of erectile dysfunction include an administration of compounds selected from the group consisting of oral PDE5 inhibitors, or local i.e. intracavernosal, intraurethral or any other penile route alprostadil. The combination with a SGLT2 inhibitor may be beneficial.

Therefore according to another aspect the present invention provides a pharmaceutical composition comprising a SGLT2 inhibitor and one or more compounds selected from the group consisting of PDE5 inhibitors or alprostadil.

According to another aspect of the invention there is provided the use of a SGLT2 inhibitor for the manufacture of a medicament for a therapeutic method as described hereinbefore and hereinafter.

According to another aspect of the invention there is provided a SGLT2 inhibitor for use in a therapeutic method as described hereinbefore and hereinafter.

According to another aspect of the invention there is provided the use of a pharmaceutical composition according to this invention for the manufacture of a medicament for a therapeutic method as described hereinbefore and hereinafter.

According to another aspect of the invention there is provided a pharmaceutical composition according to this invention for use in a therapeutic method as described hereinbefore and hereinafter.

Definitions

The term "active ingredient" of a pharmaceutical composition according to the present invention means the SGLT2 inhibitor according to the present invention. An "active ingredient is also sometimes referred to herein as an "active substance".

The term "body mass index" or "BMI" of a human patient is defined as the weight in kilograms divided by the square of the height in meters, such that BMI has units of $kg/m^2$.

The term "erectile dysfunction" is defined as the persistent inability to attain or maintain a penile erection sufficient for satisfactory sexual performance.

The term "euglycemia" is defined as the condition in which a subject has a fasting blood glucose concentration within the normal range, greater than 70 mg/dL (3.89 mmol/L) and less than 100 mg/dL (5.6 mmol/L). The word "fasting" has the usual meaning as a medical term.

The term "hyperglycemia" is defined as the condition in which a subject has a fasting blood glucose concentration above the normal range, greater than 100 mg/dL (5.6 mmol/L). The word "fasting" has the usual meaning as a medical term.

The term "hypoglycemia" is defined as the condition in which a subject has a blood glucose concentration below the normal range, in particular below 70 mg/dL (3.89 mmol/L).

The term "postprandial hyperglycemia" is defined as the condition in which a subject has a 2 hour postprandial blood glucose or serum glucose concentration greater than 200 mg/dL (11.11 mmol/L).

The term "impaired fasting blood glucose" or "IFG" is defined as the condition in which a subject has a fasting blood glucose concentration or fasting serum glucose concentration in a range from 100 to 125 mg/dl (i.e. from 5.6 to 6.9 mmol/l), in particular greater than 110 mg/dL and less than 126 mg/dl (7.00 mmol/L). A subject with "normal fasting glucose" has a fasting glucose concentration smaller than 100 mg/dl, i.e. smaller than 5.6 mmol/l.

The term "impaired glucose tolerance" or "IGT" is defined as the condition in which a subject has a 2 hour postprandial blood glucose or serum glucose concentration greater than 140 mg/dl (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dl (7.78 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-to-hip ratio <1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford E S, et al. *JAMA*. (2002) 287:356-9). A method of determining insulin resistance is the euglycaemic-hyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance.

Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., *Diabetologia* 1985, 28: 412-19), of the ratio of intact proinsulin to insulin (Forst et al., *Diabetes* 2003, 52(Suppl. 1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992; 9:921-8):

$$\text{HOMA-IR}=[\text{fasting serum insulin } (\mu U/mL)]\times[\text{fasting plasma glucose } (mmol/L)/22.5]$$

Insulin resistance can be confirmed in these individuals by calculating the HOMA-IR score. For the purpose of this invention, insulin resistance is defined as the clinical condition in which an individual has a HOMA-IR score >4.0 or a HOMA-IR score above the upper limit of normal as defined for the laboratory performing the glucose and insulin assays.

As a rule, other parameters are used in everyday clinical practice to assess insulin resistance. Preferably, the patient's triglyceride concentration is used, for example, as increased triglyceride levels correlate significantly with the presence of insulin resistance.

Individuals likely to have insulin resistance are those who have two or more of the following attributes: 1) overweight or obese, 2) high blood pressure, 3) hyperlipidemia, 4) one or more $1^{st}$ degree relative with a diagnosis of IGT or IFG or type 2 diabetes.

Patients with a predisposition for the development of IGT or IFG or type 2 diabetes are those having euglycemia with hyperinsulinemia and are by definition, insulin resistant. A typical patient with insulin resistance is usually overweight or obese. If insulin resistance can be detected, this is a particularly strong indication of the presence of pre-diabetes. Thus, it may be that in order to maintain glucose homoeostasis a person needs 2-3 times as much insulin as a healthy person, without this resulting in any clinical symptoms.

The term "overweight" is defined as the condition wherein the individual has a BMI greater than or 25 kg/m² and less than 30 kg/m². The terms "overweight" and "pre-obese" are used interchangeably.

The terms "obesity" or "being obese" and the like are defined as the condition wherein the individual has a BMI equal to or greater than 30 kg/m². According to a WHO definition the term obesity may be categorized as follows: the term "class I obesity" is the condition wherein the BMI is equal to or greater than 30 kg/m² but lower than 35 kg/m²; the term "class II obesity" is the condition wherein the BMI is equal to or greater than 35 kg/m² but lower than 40 kg/m²; the term "class III obesity" is the condition wherein the BMI is equal to or greater than 40 kg/m².

The indication obesity includes in particular exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity, central obesity, visceral obesity, abdominal obesity.

The term "PDE5 inhibitor" is defined as a phosphodiesterase type 5 inhibitor. A PDE5 inhibitor blocks the degradative action of cGMP-specific phosphodiesterase type 5 on cyclic GMP in the smooth muscle cells lining the blood vessels supplying the corpus cavernosum of the penis. PDE5 inhibitors are used in the treatment of erectile dysfunction inter alia. In a diabetic population impaired response rates in therapeutic trials with PDE5 inhibitors are observed (Hatzichristou D G. Sildenafil citrate: lessons learned from 3 years of clinical experience. Int J Impotence Res 2002; 14:S43-S51). In the scope of this invention the terms "poor-responder to a treatment with a PDE5 inhibitor" and "non-responder to a treatment with a PDE5 inhibitor" are to be understood as a patient with no sufficient result of a treatment of erectile dysfunction despite administration of a PDE5 inhibitor either on demand or daily.

Known PDE5 inhibitors include the compounds avanafil, lodenafil, mirodenafil, sildenafil, tadalafil, vardenafil, udenafil and benzamidenafil or its synthetic derivatives. The beforementioned drugs include pharmaceutically acceptable salts thereof or hydrates or solvates thereof.

The term "SGLT2 inhibitor" in the scope of the present invention relates to a compound, in particular to a glucopyranosyl-derivative, i.e. compound having a glucopyranosyl-moiety, which shows an inhibitory effect on the sodium-glucose transporter 2 (SGLT2), in particular the human SGLT2. The inhibitory effect on hSGLT2 measured as $IC_{50}$ is preferably below 1000 nM, even more preferably below 100 nM, most preferably below 50 nM. $IC_{50}$ values of SGLT2 inhibitors are usually above 0.01 nM, or even equal to or above 0.1 nM. The inhibitory effect on hSGLT2 can be determined by methods known in the literature, in particular as described in the application WO 2005/092877 or WO 2007/093610 (pages 23/24), which are incorporated herein by reference in its entirety. The term "SGLT2 inhibitor" also comprises any pharmaceutically acceptable salts thereof, hydrates and solvates thereof, including the respective crystalline forms. Examples of SGLT2 inhibitors are dapagliflozin, canagliflozin, empagliflozin, ertugliflozin, ipragliflozin, luseogliflozin, sotagliflozin, tofogliflozin, sergliflozin and remogliflozin, including prodrugs, pharmaceutically acceptable salts, hydrate and solvates thereof. Prodrugs thereof are for example remogliflozin etabonate and sergliflozin etabonate.

The term "visceral obesity" is defined as the condition wherein a waist-to-hip ratio of greater than or equal to 1.0 in men and 0.8 in women is measured. It defines the risk for insulin resistance and the development of pre-diabetes.

The term "abdominal obesity" is usually defined as the condition wherein the waist circumference is >40 inches or 102 cm in men, and is >35 inches or 94 cm in women. With regard to a Japanese ethnicity or Japanese patients abdominal obesity may be defined as waist circumference ≥85 cm in men and ≥90 cm in women (see e.g. investigating committee for the diagnosis of metabolic syndrome in Japan).

"Prediabetes" or "pre-diabetes" is a general term that refers to an intermediate stage between normal glucose tolerance (NGT) and overt type 2 diabetes mellitus (T2DM), also referred to as intermediate hyperglycaemia. As such, it represents 3 groups of individuals, those with impaired glucose tolerance (IGT) alone, those with impaired fasting glucose (IFG) alone or those with both IGT and IFG. IGT and IFG usually have distinct pathophysiologic etiologies, however also a mixed condition with features of both can exist in patients. Therefore in the context of the present invention a patient being diagnosed of having "prediabetes"

is an individual with diagnosed IGT or diagnosed IFG or diagnosed with both IGT and IFG. Following the definition according to the American Diabetes Association (ADA) and in the context of the present invention a patient being diagnosed of having "prediabetes" is an individual with:
   a) a fasting plasma glucose (FPG) concentration <100 mg/dL [1 mg/dL=0.05555 mmol/L] and a 2-hour plasma glucose (PG) concentration, measured by a 75-g oral glucose tolerance test (OGTT), ranging between ≥140 mg/dL and <200 mg/dL (i.e., IGT); or
   b) a fasting plasma glucose (FPG) concentration between ≥100 mg/dL and <126 mg/dL and a 2-hour plasma glucose (PG) concentration, measured by a 75-g oral glucose tolerance test (OGTT) of <140 mg/dL (i.e., IFG); or
   c) a fasting plasma glucose (FPG) concentration between ≥100 mg/dL and <126 mg/dL and a 2-hour plasma glucose (PG) concentration, measured by a 75-g oral glucose tolerance test (OGTT), ranging between ≥140 mg/dL and <200 mg/dL (i.e., both IGT and IFG).

Patients with "prediabetes" are individuals being predisposed to the development of type 2 diabetes. Prediabetes extends the definition of IGT to include individuals with a fasting blood glucose within the high normal range ≥100 mg/dL (J. B. Meigs, et al. Diabetes 2003; 52:1475-1484). The scientific and medical basis for identifying prediabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

The methods to investigate the function of pancreatic beta-cells are similar to the above methods with regard to insulin sensitivity, hyperinsulinemia or insulin resistance: An improvement of beta-cell function can be measured for example by determining a HOMA-index for beta-cell function (Matthews et al., *Diabetologia* 1985, 28: 412-19), the ratio of intact proinsulin to insulin (Forst et al., *Diabetes* 2003, 52(Suppl. 1): A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur J Clin Invest* 2001, 31: 380-81).

The term "type 2 diabetes mellitus" or "T2DM" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage type 2 diabetes mellitus" includes patients with a secondary drug failure, indication for insulin therapy and progression to micro- and macrovascular complications e.g. diabetic nephropathy, or coronary heart disease (CHD).

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks. Diabetic patients whose HbA1c value is consistently well adjusted by intensive diabetes treatment (i.e. <6.5% of the total haemoglobin in the sample), are significantly better protected against diabetic microangiopathy. For example, metformin on its own achieves an average improvement in the HbA1c value in the diabetic of the order of 1.0-1.5%. This reduction of the HbA1C value is not sufficient in all diabetics to achieve the desired target range of <6.5% and preferably <6% HbA1c.

The term "insufficient glycemic control" or "inadequate glycemic control" in the scope of the present invention means a condition wherein patients show HbA1c values above 6.5%, in particular above 7.0%, even more preferably above 7.5%, especially above 8%.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference >40 inches or 102 cm in men, and >35 inches or 94 cm in women; or with regard to a Japanese ethnicity or Japanese patients defined as waist circumference ≥85 cm in men and ≥90 cm in women;
2. Triglycerides: ≥150 mg/dL
3. HDL-cholesterol <40 mg/dL in men
4. Blood pressure ≥130/85 mm Hg (SBP ≥130 or DBP ≥85)
5. Fasting blood glucose ≥100 mg/dL The NCEP definitions have been validated (Laaksonen D E, et al. *Am J Epidemiol*. (2002) 156:1070-7). Triglycerides and HDL cholesterol in the blood can also be determined by standard methods in medical analysis and are described for example in Thomas L (Editor): "Labor and Diagnose", TH-Books Verlagsgesellschaft mbH, Frankfurt/Main, 2000.

According to a commonly used definition, hypertension is diagnosed if the systolic blood pressure (SBP) exceeds a value of 140 mm Hg and diastolic blood pressure (DBP) exceeds a value of 90 mm Hg. If a patient is suffering from manifest diabetes it is currently recommended that the systolic blood pressure be reduced to a level below 130 mm Hg and the diastolic blood pressure be lowered to below 80 mm Hg.

The term "empagliflozin" refers to the SGLT2 inhibitor 1-chloro-4-(β-D-glucopyranos-1-yl)-2-[4-((S)-tetrahydrofuran-3-yloxy)-benzyl]-benzene of the formula as described for example in WO 2005/092877. Methods of synthesis are described in the literature, for example WO 06/120208 and WO 2011/039108. According to this invention, it is to be understood that the definition of empagliflozin also comprises its hydrates, solvates and polymorphic forms thereof, and prodrugs thereof. An advantageous crystalline form of empagliflozin is described in WO 2006/117359 and WO 2011/039107 which hereby are incorporated herein in their entirety. This crystalline form possesses good solubility properties which enables a good bioavailability of the SGLT2 inhibitor. Furthermore, the crystalline form is physico-chemically stable and thus provides a good shelf-life stability of the pharmaceutical composition. Preferred pharmaceutical compositions, such as solid formulations for oral administration, for example tablets, are described in WO 2010/092126, which hereby is incorporated herein in its entirety.

The terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. The term treatment also encompasses prophylactically treating, preventivally treating and preventing also. These terms are used interchangeably and comprise a treatment of patients at risk to develop a condition mentioned hereinbefore, thus reducing said risk.

The term "tablet" comprises tablets without a coating and tablets with one or more coatings. Furthermore the "term" tablet comprises tablets having one, two, three or even more layers and press-coated tablets, wherein each of the beforementioned types of tablets may be without or with one or more coatings. The term "tablet" also comprises mini, melt, chewable, effervescent and orally disintegrating tablets.

The terms "pharmacopoe" and "pharmacopoeias" refer to standard pharmacopoeias such as the "USP 31-NF 26 through Second Supplement" (United States Pharmacopeial Convention) or the "European Pharmacopoeia 6.3" (European Directorate for the Quality of Medicines and Health Care, 2000-2009).

BRIEF DESCRIPTION OF THE FIGURES

The FIG. 3 shows relaxant responses elicited by increasing frequencies of EFS on PHE-induced contractions of CC strips from Wistar rats

DETAILED DESCRIPTION

The aspects according to the present invention, in particular the pharmaceutical compositions, methods and uses, refer to a SGLT2 inhibitor as defined hereinbefore and hereinafter.

According to an embodiment of this invention the SGLT2 inhibitor is selected from the group consisting of dapagliflozin, canagliflozin, empagliflozin, ertugliflozin, ipragliflozin, luseogliflozin, sotagliflozin, tofogliflozin, sergliflozin and remogliflozin, including prodrugs, pharmaceutically acceptable salts, hydrate and solvates thereof. Prodrugs thereof are for example remogliflozin etabonate and sergliflozin etabonate.

According to a particularly preferred embodiment the SGLT2 inhibitor is empagliflozin.

The aspects according to the present invention, in particular the methods and uses, refer to a treatment of patients diagnosed with prediabetes, type 1 diabetes mellitus, type 2 diabetes mellitus or metabolic syndrome as defined hereinbefore and hereinafter.

According to an embodiment of this invention the patient is diagnosed with type 2 diabetes mellitus.

According to another embodiment of this invention the patient is diagnosed with type 1 diabetes mellitus.

According to a further embodiment of this invention the patient is diagnosed with prediabetes.

According to a further embodiment of this invention the patient is diagnosed with metabolic syndrome.

When this invention refers to patients requiring treatment or prevention, it relates primarily to treatment and prevention in male humans, in particular in adult male humans, but the pharmaceutical composition may also be used accordingly in veterinary medicine in mammals. In the scope of this invention adult patients are preferably humans of the age of 18 years or older.

According to an embodiment of this invention the patient has insufficient glycemic control with diet and exercise alone.

In view of the insulin-independent mode of action the efficacy of a SGLT2 inhibitor is maintained even in patients with decreased beta-cell activity. Thus in patients with insufficient glycemic control under treatment with other antidiabetic drugs, a treatment with a SGLT2 inhibitor still leads to a lowering of blood glucose. Therefore according to an embodiment of this invention the patient has insufficient glycemic control despite antidiabetic treatment with one or more medicaments not including SGLT2 inhibitors. In particular the patient has insufficient glycemic control despite oral treatment with one, two or more drugs selected from the group consisting of metformin hydrochloride and sulfonylureas. For example the patient has insufficient glycemic control despite oral monotherapy with metformin hydrochloride, in particular despite oral monotherapy at a maximal recommended or tolerated dose of metformin hydrochloride.

According to an embodiment of this invention the patient is over the age of 60 years. It is known that the frequency of erectile dysfunction increases with age.

In a diabetic population impaired response rates in therapeutic trials with PDE5 inhibitors are observed. In view of an independent mode of action of SGLT2 inhibitors patients poorly or not responding to a treatment with a PDE5 inhibitor may still benefit from a pro-erectile effect resulting from an administration of a SGLT2 inhibitor. Therefore according to an embodiment of this invention the patient is a poor-responder or a non-responder to a treatment with a PDE5 inhibitor, in particular to a treatment with a compound selected from the group consisting of avanafil, lodenafil, mirodenafil, sildenafil, tadalafil, vardenafil, udenafil and benzamidenafil or a pharmaceutically acceptable salts thereof or hydrates or solvates thereof.

SGLT2 inhibitors, in particular empagliflozin, were shown to have a weight reducing effect. Therefore according to an embodiment of this invention the patient is diagnosed of being overweight or obese, including class I, II and/or III obesity, visceral obesity and/or abdominal obesity.

According to an embodiment of this invention the patient is diagnosed with type 2 diabetes and overweight or obese, including class I, II and/or III obesity, visceral obesity and/or abdominal obesity.

According to another embodiment of this invention the patient is diagnosed with type 1 diabetes and overweight or obese, including class I, II and/or III obesity, visceral obesity and/or abdominal obesity.

According to a further embodiment of this invention the patient is diagnosed with prediabetes and overweight or obese, including class I, II and/or III obesity, visceral obesity and/or abdominal obesity.

The present invention also discloses methods and uses for improving glycemic control in patients being overweight or obese and having type 2 diabetes or showing first signs of pre-diabetes. Thus, the invention also includes diabetes prevention. If therefore a pharmaceutical composition according to this invention is used to improve the glycemic control as soon as one of the above-mentioned signs of pre-diabetes are present in an overweight or obese patient, the onset of manifest type 2 diabetes mellitus can be delayed or prevented in this patient.

According to an embodiment of this invention the methods or uses according to this invention are advantageously applicable in those patients who show one, two or more of the following conditions:
  (a) a fasting blood glucose or serum glucose concentration greater than 100 mg/dL, in particular greater than 125 mg/dL;
  (b) a postprandial plasma glucose equal to or greater than 140 mg/dL;
  (c) an HbA1c value equal to or greater than 6.5%, in particular equal to or greater than 7.0%, especially equal to or greater than 7.5%, even more particularly equal to or greater than 8.0%.

According to an embodiment of this invention the methods or uses according to this invention is particularly suitable in the treatment of patients who are diagnosed of being overweight or obese and having one or more of the following conditions
  (a) triglyceride blood level ≥150 mg/dL,
  (b) HDL-cholesterol blood level <40 mg/dL in female patients and <50 mg/dL in male patients,
  (c) a systolic blood pressure ≥130 mm Hg and a diastolic blood pressure ≥85 mm Hg,
  (d) a fasting blood glucose level ≥100 mg/dL.

A method for treatment or use according to this invention is particularly suitable as long term treatment or use as described hereinbefore and hereinafter, in particular in patients diagnosed with erectile dysfunction and diagnosed with prediabetes, type 1 diabetes mellitus or type 2 diabetes mellitus. The term "long term" as used hereinbefore and hereinafter indicates a treatment of or administration in a patient within a period of time longer than 8 weeks, preferably longer than 12 weeks, more preferably longer than 25 weeks or longer than 1 year.

According to an aspect the present invention provides a method for improving a treatment of erectile dysfunction in a male patient diagnosed with prediabetes, type 1 diabetes mellitus, type 2 diabetes mellitus or metabolic syndrome characterized in that in addition to the treatment of erectile dysfunction a SGLT2 inhibitor is administered to the patient.

According to an embodiment of this aspect of the invention the treatment of erectile dysfunction comprises an administration of one or more medicaments selected from the group consisting of PDE5 inhibitors, or alprostadil. The beforementioned drugs include pharmaceutically acceptable salts thereof or hydrates or solvates thereof.

According to an embodiment of this aspect of the invention the PDE5 inhibitor is selected from the group consisting of avanafil, lodenafil, mirodenafil, sildenafil, tadalafil, vardenafil, udenafil, benzamidenafil or its synthetic derivatives. Preferred PDE5 inhibitors are avanafil, sildenafil, tadalafil and vardenafill. The beforementioned drugs include pharmaceutically acceptable salts thereof or hydrates or solvates thereof.

Preferred SGLT2 inhibitors according to this aspect of the invention are those as described hereinbefore. A particularly preferred SGLT2 inhibitor is empagliflozin.

In the following, preferred ranges of the amount of active ingredients to be employed in the methods and uses according to this invention are described. These ranges refer to the amounts to be administered per day with respect to an adult patient, in particular to a human being, for example of approximately 70 kg body weight, and can be adapted accordingly with regard to an administration 2 times daily and with regard to other routes of administration and with regard to the age of the patient. The ranges of the dosage and amounts are calculated for the active ingredient.

A preferred amount of empagliflozin is in a range from 1 to 50 mg, even more preferably from 2.5 to 25 mg, even more preferably 5 to 25 mg for once daily oral administration. Preferred dosages of empagliflozin are for example 2 mg, 2.5 mg, 5 mg, 10 mg, 12.5 mg, 15 mg, 20 mg and 25 mg for once daily oral administration. Most preferred dosages of empagliflozin are 10 mg and 25 mg for once daily oral administration. Tablet formulations of empagliflozin are described in WO 2010/092126 which is incorporated herein by reference. Empagliflozin tablet formulations are marketed under the tradename JARDIANCE.

A preferred amount of dapagliflozin is in a range from 1 to 50 mg, even more preferably from 2.5 to 25 mg, even more preferably 5 to 20 mg for once daily oral administration. Preferred dosages of dapagliflozin are for example 5 mg and 10 mg for once daily oral administration. Tablet formulations of dapagliflozin are marketed under the tradename FORXIGA.

A preferred amount of canagliflozin is in a range from 50 to 500 mg, even more preferably from 100 to 300 mg for once daily oral administration. Preferred dosages of canagliflozin are for example 100 mg and 300 mg for once daily oral administration. Tablet formulations of canagliflozin are marketed under the tradename INVOKANA.

According to an embodiment of this invention the SGLT2 inhibitor is administered together with another antidiabetic drugs. According to a preferred variant of this embodiment the SGLT2 inhibitor is administered together with metformin hydrochloride. According to another variant of this embodiment the SGLT2 inhibitor is administered together with a DPPIV inhibitor. Examples of DPPIV inhibitors are linagliptin, sitagliptin, saxagliptin and vildagliptin. The beforementioned drugs include pharmaceutically acceptable salts thereof or hydrates or solvates thereof.

According to an example of this embodiment empagliflozin is administered together with metformin hydrochloride. The administration of empagliflozin may be an add-on to an existing treatment with metformin hydrochloride or a fixed dose combination of empagliflozin with metformin hydrochloride is administered. Metformin hydrochloride may be administered as an immediate or extended release formulation. Examples of individual amounts for a combination of empagliflozin/metformin hydrochloride are 5 mg/500 mg, 5 mg/850 mg, 5 mg/1000 mg, 12.5 mg/500 mg, 12.5 mg/850 mg and 12.5 mg/1000 mg each for twice daily oral administration, wherein metformin chloride is present in an immediate release formulation. Tablet formulations of fixed dose combinations of empagliflozin with metformin hydrochloride as immediate release formulation are described in WO 2011/039337 which is incorporated herein by reference. According to another example amounts for a combination of empagliflozin/metformin hydrochloride are 10 mg/1000 mg and 25 mg/1000 mg each for once daily oral administration, wherein metformin chloride is present in an extended release formulation. According to yet another example amounts for a combination of empagliflozin/metformin hydrochloride are 5 mg/1000 mg and 12.5 mg/1000 mg each for twice daily oral administration, wherein metformin chloride is present in an extended release formulation. Tablet formulations of fixed dose combinations of empagliflozin with metformin hydrochloride as extended release formulation are described in WO 2012/120040 and WO 2013/131967 which are incorporated herein by reference.

According to another example of this embodiment empagliflozin is administered together with the DPPIV inhibitor linagliptin or a pharmaceutically acceptable salt thereof. The administration of empagliflozin and linagliptin may be separately in two separate dosage forms or a fixed dose combination of empagliflozin with linagliptin. Examples of individual amounts for a combination of empagliflozin/linagliptin are 10 mg/5 mg and 25 mg/5 mg each for once daily oral administration. Respective tablet formulations are described in WO 2010/092124 which is incorporated herein by reference.

According to another example of this embodiment dapagliflozin is administered together with metformin hydrochloride. The administration of dapagliflozin may be an add-on to an existing treatment with metformin hydrochloride or a fixed dose combination of dapagliflozin with metformin hydrochloride is administered. Metformin hydrochloride may be administered as an immediate or extended release formulation. Examples of individual amounts for a combination of dapagliflozin/metformin hydrochloride are 5 mg/850 mg and 5 mg/1000 mg each for twice daily oral administration, wherein metformin chloride is present in an immediate release formulation. Tablet formulations of dapagliflozin together with metformin hydrochloride as immediate release formulation are marketed under the tradename XIGDUO.

According to yet another example of this embodiment canagliflozin is administered together with metformin hydrochloride. The administration of canagliflozin may be an add-on to an existing treatment with metformin hydrochloride or a fixed dose combination of canagliflozin with metformin hydrochloride is administered. Metformin hydrochloride may be administered as an immediate or extended release formulation. Examples of individual amounts for a combination of canagliflozin/metformin hydrochloride are 50 mg/850 mg, 150 mg/850 mg, 50 mg/1000 mg and 150 mg/1000 mg each for twice daily oral administration, wherein metformin chloride is present in an immediate release formulation. Tablet formulations of canagliflozin together with metformin hydrochloride as immediate release formulation are marketed under the tradename VOKANAMET.

According to another variant of the hereinbefore described embodiment the SGLT2 inhibitor is administered together with an insulin. The term insulin includes normal insulin, human insulin, insulin derivatives, zinc insulins and insulin analogues, including formulations thereof with modified release profiles. The term insulin covers rapid-acting insulins, short-acting insulins, intermediate-acting insulins and long-acting insulins. Patients which may benefit from an administration of a SGLT2 inhibitor and insulin according to this invention are patients diagnosed with type 1 diabetes mellitus. Furthermore patients which may benefit from an administration of a SGLT2 inhibitor and insulin according to this invention are patients with type 2 diabetes mellitus, in particular type 2 diabetes mellitus patients with insufficient glycemic control despite therapy with one or more oral antidiabetic drugs.

According to an embodiment of this aspect of the invention the treatment of erectile dysfunction comprises an administration of one or more medicaments selected from the group consisting of PDE5 inhibitors or alprostadil, in particular selected from the group consisting of avanafil, sildenafil, tadalafil and vardenafil. The beforementioned drugs include pharmaceutically acceptable salts thereof or hydrates or solvates thereof.

A preferred amount of sildenafil is in a range from 25 to 100 mg on demand for oral administration. Preferred dosages of sildenafil are for example 25 mg, 50 mg and 100 mg. The dose is taken as needed before sexual activity, for example approximately one hour before sexual activity. Tablet formulations of sildenafil are marketed under the tradename VIAGRA for example.

A preferred amount of tadalafil is in a range from 1 to 100 mg, even more preferably from 2.5 and 5 to 20 mg once per day for oral administration. Preferred dosages of tadalafil are for example 2.5 mg, 5 mg, 10 mg and 20 mg. Tadalafil 2.5 and 5 mg are doses for once a day treatment for erectile dysfunction. The dose is taken prior to anticipated sexual activity. Tablet formulations of tadalafil are marketed under the tradename CIALIS for example.

A preferred amount of vardenafil is in a range from 1 to 50 mg, even more preferably from 5 to 20 mg once per day for oral administration. Preferred dosages of vardenafil are for example 5 mg, 10 mg and 20 mg. Vardenafil is provided preferably as a pharmaceutically acceptable salt, in particular as the hydrochloride. The dose is taken as needed before sexual activity, for example approximately 25 to 60 minutes before sexual activity. Tablet formulations of vardenafil are marketed under the tradename LEVITRA or VIVANZA for example. There is also an oral dispersable formulation for vardenafil (Levitra ODT).

Unless otherwise noted, the combination therapy according to the invention may refer to first line, second line or third line therapy, or initial or add-on combination therapy or replacement therapy.

According to one embodiment SGLT2 inhibitor and the medicament selected from the group consisting of PDE5 inhibitors are administered in combination, i.e. simultaneously, for example in one single formulation or dosage form or in two separate formulations or dosage forms, or in alternation or sequentially, for example successively in two separate formulations or dosage forms. Hence, the administration of one combination partner, i.e. the SGLT2 inhibitor or the PDE5 inhibitor, may be prior to, concurrent to, or subsequent to the administration of the other combination partner. In one embodiment, for the combination therapy according to this invention the SGLT2 inhibitor and the PDE5 inhibitor are administered in different formulations or different dosage forms. In another embodiment, for the combination therapy according to this invention the SGLT2 inhibitor and the PDE5 inhibitor are administered in the same formulation or in the same dosage form.

In the methods and uses according to the present invention the SGLT2 inhibitor and the PDE5 inhibitor are administered in combination or alternation or sequentially. The term "administration in combination" means that the active ingredients are administered at the same time, i.e. simultaneously, or essentially at the same time. The term "administration in alternation" means that at first one of the two active ingredients, i.e. the SGLT2 inhibitor or the PDE5 inhibitor, is administered and after a period of time the other active ingredient, i.e. the PDE5 inhibitor or the SGLT2 inhibitor, is administered whereby this administration scheme may be repeated one or more times. The period of time between the administration of the first and of the second active ingredient may be in the range from 1 min to 12 hours. The administration which is in combination or in alternation may be once, twice, three times or four times daily, preferably once or twice daily. The term "sequentially" means that to a patient the first active ingredient is administered to the patient one or more times in a first period of time followed by an administration of the second active ingredient which is administered to the patient one or more times in a second period of time.

According to an embodiment of the methods and uses of the present invention the SGLT2 inhibitor is administered to the patient once per day and the PDE5 inhibitor is administered before sexual activity.

According to an aspect the present invention provides a pharmaceutical composition comprising a SGLT2 inhibitor and one or more compounds selected from the group consisting of PDE5 inhibitors or alprostadil.

Preferred SGLT2 inhibitors are as described hereinbefore. The most preferred SGLT2 inhibitor is empagliflozin.

PDE5 inhibitors according to this invention are described hereinbefore. Preferred PDE5 inhibitors are sildenafil, tadalafil, vardenafil and avanafil. The beforementioned drugs include pharmaceutically acceptable salts thereof or hydrates or solvates thereof.

According to an embodiment of this invention the pharmaceutical composition comprises one or more pharmaceutically acceptable excipients.

According to an embodiment of the present invention there is provided a pharmaceutical dosage form comprising empagliflozin and a PDE5 inhibitor and one or more pharmaceutically acceptable excipients.

The amount of the SGLT2 inhibitor in the pharmaceutical compositions and pharmaceutical dosage forms according to this invention are known to the one skilled in the art and/or correspond to the respective dosage ranges as provided hereinbefore.

The amount of the PDE5 inhibitor in the pharmaceutical compositions and pharmaceutical dosage forms according to this invention are known to the one skilled in the art and/or correspond to the respective dosage ranges as provided hereinbefore.

According to an embodiment the pharmaceutical composition or the pharmaceutical dosage form is provided for oral administration.

A pharmaceutical composition which is present as a separate or multiple dosage form, for example as a kit of parts, is useful in combination therapy to flexibly suit the individual therapeutic needs of the patient. For example a pharmaceutical composition may be present as a first pharmaceutical dosage form comprising the SGLT2 inhibitor and one or more pharmaceutically excipients and a second pharmaceutical dosage form comprising the PDE5 inhibitor, apomorphin or alprostadil and one or more pharmaceutically excipients According to an embodiment of the invention a kit of parts comprises
  (a) a first containment containing a dosage form comprising the SGLT2 inhibitor and one or more pharmaceutically acceptable excipients, and
  (b) a second containment containing a dosage form comprising the PDE5 inhibitor, apomorphin or alprostadil and one or more pharmaceutically acceptable excipients.

Within the scope of the present invention, the SGLT2 inhibitor is preferably administered orally or by injection, preferably orally. The PDE5 inhibitor is preferably administered orally. Alprostadil is preferably administered by intracavernosal injection. Other forms of administration are possible and described for the respective drug in the literature.

The effects mentioned above are observed both, when SGLT2 inhibitor and the PDE5 inhibitor or alprostadil are administered in combination, for example simultaneously in one single or two separate pharmaceutical dosage forms, and when they are administered in alternation, for example successively in two or three separate pharmaceutical dosage forms.

It will be appreciated that the amount of the pharmaceutical composition according to this invention to be administered to the patient and required for use in treatment or prophylaxis according to the present invention will vary with the route of administration, the nature and severity of the condition for which treatment or prophylaxis is required, the age, weight and condition of the patient, concomitant medication and will be ultimately at the discretion of the attendant physician. In general, however, the SGLT2 inhibitor according to this invention is included in the pharmaceutical composition or dosage form in an amount sufficient that by its administration the glycemic control in the patient to be treated is improved. Furthermore in general, the PDE5 inhibitor or alprostadil according to this invention are included in the pharmaceutical composition or dosage form in an amount sufficient that by their administration in combination with the SGLT2 inhibitor the erectile function in the patient to be treated is improved.

The amount of the SGLT2 inhibitor and the PDE5 inhibitor or alprostadil in the pharmaceutical compositions and pharmaceutical dosage forms according to this invention correspond to the respective dosage ranges as provided hereinbefore.

The desired dose of the pharmaceutical composition according to this invention may conveniently be presented in a once daily or as divided dose administered at appropriate intervals, for example as two, three or more doses per day. Once daily administration is preferred.

The pharmaceutical composition may be formulated for oral, parenteral (including sub-cutaneous) or other routes of administration in liquid or solid form. Oral administration of the SGLT2 inhibitor is preferred. The formulations may, where appropriate, be conveniently presented in discrete dosage units and may be prepared by any of the methods well known in the art of pharmacy. All methods include the step of bringing into association the active ingredient with one or more pharmaceutically acceptable excipients, such as carriers, like liquid carriers or finely divided solid carriers or both, or diluents, and then, if necessary, shaping the product into the desired formulation. Examples of pharmaceutical compositions and pharmaceutical dosage forms comprising empagliflozin and one or more pharmaceutically acceptable excipients are described in WO 2010/092126.

The pharmaceutical composition and the pharmaceutical dosage form preferably comprises one or more pharmaceutical acceptable excipients. Preferred excipients must be "acceptable" in the sense of being compatible with the other ingredients of the formulation and not deleterious to the recipient thereof. Examples of pharmaceutically acceptable excipients are known to the one skilled in the art.

The pharmaceutical composition may be formulated in the form of solutions, suspensions, emulsions, tablets, granules, fine granules, powders, capsules, caplets, soft capsules, pills, oral solutions, syrups, dry syrups, chewable tablets, troches, effervescent tablets, drops, fast dissolving tablets, oral fast-dispersing tablets, etc. According to a preferred embodiment of the present invention there is provided a solid pharmaceutical composition for oral administration. Preferred pharmaceutical dosage form are tablets or capsules.

For further details on dosage forms, formulations and administration of the SGLT2 inhibitor and/or the PDE5 inhibitor or alprostadil, reference is made to scientific literature and/or published patent documents, particularly to those cited herein.

The pharmaceutical composition or dosage form may be packaged in a variety of ways. Generally, a manufacture or an article for distribution includes one or more containers that contain the one or more pharmaceutical dosage forms in an appropriate form. Tablets are typically packed in an appropriate primary package for easy handling, distribution and storage and for assurance of proper stability of the composition at prolonged contact with the environment during storage. Primary containers for tablets may be bottles or blister packs.

The manufacture or article may further comprise a label or package insert, which refers to instructions customarily included in commercial packages of therapeutic products, that may contain information about the indications, usage, dosage, administration, contraindications and/or warnings concerning the use of such therapeutic products. In one embodiment, the label or package inserts indicates that the composition can be used for any of the purposes described hereinbefore or hereinafter.

An aspect of the present invention is a manufacture comprising the pharmaceutical composition being present as a pharmaceutical dosage form comprising the SGLT2 inhibitor and a PDE5 inhibitor or alprostadil and one or more pharmaceutically acceptable excipients.

A further aspect of the present invention is a manufacture comprising the pharmaceutical composition being present as a first and a second pharmaceutical dosage form according to the present invention and a label or package insert comprising instructions that the first and the second pharmaceutical dosage forms are to be administered in combination or alternation or sequentially. Herein the first pharmaceutical dosage form comprises the SGLT2 inhibitor and one or more pharmaceutically excipients and the second pharmaceutical dosage form comprises a PDE5 inhibitor or alprostadil and one or more pharmaceutically excipients.

According to a first embodiment a manufacture comprises (a) a pharmaceutical composition, in particular a solid pharmaceutical dosage form for oral administration, comprising the SGLT2 inhibitor according to the present invention and one or more pharmaceutically acceptable excipients and (b) a label or package insert which comprises instructions that the pharmaceutical composition may or is to be administered, for example in combination or alternation or sequentially, with a medicament comprising a PDE5 inhibitor or alprostadil according to the present invention.

According to a second embodiment a manufacture comprises (a) a pharmaceutical composition comprising PDE5 inhibitor or alprostadil and one or more pharmaceutically acceptable excipients and (b) a label or package insert which comprises instructions that the pharmaceutical composition may or is to be administered, for example in combination or alternation or sequentially, with a medicament comprising the SGLT2 inhibitor according to the present invention according to the present invention.

The pharmaceutical compositions, dosage forms, methods and uses according to this invention show advantageous effects in the treatment and prevention of those diseases and conditions as described hereinbefore compared with pharmaceutical compositions, dosage forms, methods and uses which comprise only one of the two active ingredients. Additional advantageous effects may be seen for example with respect to efficacy, dosage strength, dosage frequency, pharmacodynamic properties, pharmacokinetic properties, fewer adverse effects, convenience, compliance, etc.

Any of the above mentioned combinations, methods and uses within the scope of the invention may be tested by animal models known in the art. In the following, in vivo experiments are described which are suitable to evaluate pharmacologically relevant properties of methods, uses and pharmaceutical compositions according to this invention:

Pharmaceutical compositions and methods according to this invention can be tested in experimental model of erectile or diabetic animals like db/db mice, ob/ob mice, Zucker Fatty (fa/fa) rats or Zucker Diabetic Fatty (ZDF) rats. In addition, they can be tested in animals with experimentally induced diabetes like HanWistar or Sprague Dawley rats pretreated with streptozotocin.

The effect on glycemic control of the combinations according to this invention can be tested in an oral glucose tolerance test in the animal models described hereinbefore. The time course of blood glucose is followed after an oral glucose challenge in overnight fasted animals. In addition an improvement of glucose excursion can be measured by reduction of peak glucose concentrations or reduction of glucose AUC. The effect on glycemic control can be determined by measuring the HbA1c value in blood.

PHARMACOLOGICAL EXAMPLES

The following examples show the beneficial effect of empagliflozin on erectile function in a well-established in vivo model of erectile dysfunction (ED) associated to type II diabetes i.e., Goto-kakizaki diabetic rats (GK rats).

Example 1

Animal In Vivo Experiments

Animals

Goto-Kakizaki (GK) rats has been shown to be a relevant experimental model of type II diabetes mellitus-associated erectile dysfunction. It was shown that erectile function in GK rats was markedly impaired (Oger-Roussel S, Behr-Roussel D, Caisey S, Kergoat M, Charon C, Audet A, Bernabe J, Alexandre L, Giuliano F. Bladder and erectile dysfunctions in the Type 2 diabetic Goto-Kakizaki rat. Am J Physiol Regul Integr Comp Physiol 2014; 306:R108-R117). In that model, the impaired erectile function was partially improved by an acute single dose (0.3 mg/kg) of the PDE5 inhibitor sildenafil. Thus, GK rats represent a suitable model to investigate the pathophysiology of type 2 diabetes-associated erectile complications and to assess efficacy of new therapeutic agents targeting diabetic ED.

Methods

Adult male Wistar (Charles River, France) and age-matched GK rats (Metabrain Research, Chilly-Mazarin, France) were housed at least 7 days prior to the beginning of the treatment with free access to control diet and water and maintained on an inversed 12 h dark/light cycle. At 15 weeks of age, treatments were started; n=12 Wistar (group I) rats and n=24 GK (group II) rats were fed with a control diet, while n=24 GK rats (group III) were fed for 28 days by a medicated diet i.e., control diet premixed with empagliflozin 300 ppm (parts per million corresponding to an average of 25.3 mg/kg body weight of empaglfilozin in that experiment).

On day $29^{th}$ after starting treatment administration, and approximately 16 hours after the last treatment administration, fasted rats (19 weeks of age) underwent an in vivo evaluation of their erectile function after electrical stimulation of the cavernous nerve (ES CN), in comparison to acute dosing of sildenafil.

Erectile responses were elicited by electric stimulation (ES) of the cavernous nerve (CN) and measured by monitoring intracavernous pressure (ICP) in anesthetized rats according to an experimental procedure previously described and well-standardized. After an overnight fasting period, rats were anesthetized (urethane 1.2 mg/kg) and their temperature maintained at 37° C. using a homoeothermic blanket. A tracheotomy was performed to prevent aspiration of saliva and to perform, when required, artificial ventilation. The carotid artery was catheterized with polyethylene tubings filled with heparinized saline (25 UI/ml) to record blood pressure (BP) via a pressure transducer (Elcomatic 750, Glasgow, UK). Simultaneous computerized measure of BP and ICP was performed. CN was exposed at the lateral aspect of the prostate, with the aid of a dissecting microscope and mounted on a bipolar platinum electrode connected to an electrical stimulator (AMS 2100, Phymep, France). In some animals an acute dose of sildenafil (0.3 mg/kg) or vehicle was intravenously injected. This dose of sildenafil has previously been demonstrated to ameliorate erectile function in anesthetized GK rats (ref OGER-ROUSSEL S., BEHR-ROUSSEL D., CAISEY S., KERGOAT M., CHARON C., AUDET A., BERNABÉ J., ALEXANDRE L., GIULIANO F., Bladder and erectile dysfunctions in the type 2 diabetic Goto-Kakizaki rat, Am. J. Physiol. Regul. Integr. Comp. Physiol. 2014; 306(2):R108-17). The CN was stimulated at 6V, 1 ms for 45 s by different stimulation frequencies (0, 2.5, 5, 7.5, 10, 12.5 and 15 Hz) in a randomized manner in order to assess the erectile responses. These different electrical stimulations on the increase of ICP were repeated twice in view of establishing a frequency-response curve for each animal.

Mean arterial pressure (MAP) and the amplitude of the erectile responses elicited by each ES CN were quantified for each rat and averaged for each experimental group by calculating:

ICP (mmHg)/MAP (mmHg)×100 with AICP being the difference between ICP in the flaccid state, i.e. before stimulation and ICP during the plateau phase of the erectile response, and MAP, the mean arterial pressure during the plateau phase.

$AUC_{45}$/MAP with $AUC_{45}$, the area under the curve during the first 45 seconds after the beginning of the electrical stimulation of the cavernous nerve and determined using the ICP level in the flaccid state before the onset of the stimulation.

$AUC_{tot}$/MAP with $AUC_{tot}$, the area under the curve during the entire erectile response, measured from the beginning of the electrical stimulation until the end of the erectile response and determined using the ICP level in the flaccid state before the onset of the stimulation.

ICP increase and AUC were normalized with MAP to account for the close influence of the systemic blood pressure in the amplitude of ICP increase during the plateau phase of the erectile response.

In addition, to further evaluate erectile function, at the end of the in vivo evaluation of the ED, the penis of 24 GK rats (groups IIA & IIIA) and 12 wistar rats (group I) were immediately harvested and the corpora cavernosa (CC) dissected for ex vivo isometric tension studies. After extensive washings, corporal strips were incubated in the presence of guanethidine (5 μM) and atropine (1 μM) that were also added to the organ chambers for the remainder of the experiments. The corporal strips were placed between two parallel platinum electrodes in the organ baths. After equilibration (60 min), the electric field stimulation (EFS) experiments were started. Firstly, a priming period was observed where corporal strips from Wistar, GK (control) and GK_Chronic empa were exposed to phenylephrine (PHE) ($10^{-5}$ M) followed by an EFS-induced relaxation at 1 ms, 10 s, 300 mA and 20 Hz. Then, after washings, frequency-response curves (FRC) to EFS (1-2-4-8-16-32 Hz) was constructed on PHE-precontracted corporal strips (PHE $10^{-5}$ M). Frequency response-curves (FRC) to EFS were performed by successive stimulation of the corporal strips at 1 ms, 10 s, 300 mA and increasing frequencies (1, 2, 4, 8, 16 and 32 Hz).

Statistical Analysis

All results are presented as mean±SEM. Grubbs test was used for the detection and exclusion of outliers. This statistical method allowed determining when a value was unlikely to have come from the same Gaussian population as the other values in the group.

For erectile function evaluation, comparisons of frequency-response curves were performed with a two-way ANOVA statistical analysis test followed by a Bonferroni's post-test. In case of significant interaction between the two factors (i.e. frequency of ES CN and experimental group), the difference between groups of rats was examined by the modified Student's t-test with the Bonferroni's adjustment for multiple comparisons.

For organ bath experiments, the amplitude of EFS-induced relaxations were expressed in percentage of inhibition of the contractile response to PHE.

The results from duplicate determinations in one experiment with CC from one rat were averaged and the data expressed as mean±SEM for N experiments using CC from N different rats.

Statistical comparisons FRCs were performed using a two-way ANOVA statistical analysis test and Bonferroni's post-test.

Statistical analysis was performed with GraphPad Prism® 5.04 software. P values<0.05 are considered significant.

Results

In the following an effect of chronic treatment with empagliflozin on in vivo erectile function in GK rats is described in comparison to an acute administration of sildenafil.

Figure 1:
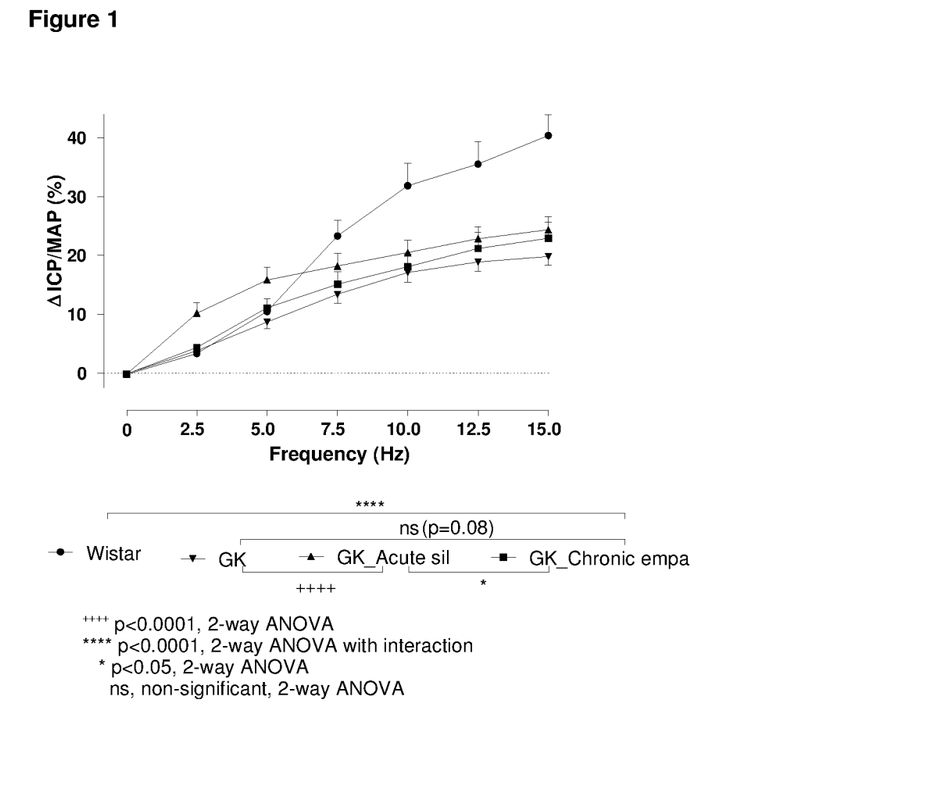
FIG. 1 shows erectile responses elicited by cavernous nerve stimulation at increasing stimulation frequencies in animals.

The FIG. 1 shows erectile responses elicited by cavernous nerve stimulation at increasing stimulation frequencies in anaesthetized Wistar rats that received control diet and acute injection of normal saline (WI, n=15), GK rats that received control diet and acute injection of normal saline (GK, n=10) or sildenafil at 0.3 mg/kg (GK_Acute sil, n=12) and GK rats that received medicated diet i.e., control diet premixed with empagliflozin at 25.3±0.9 mg/kg/day, and acute injection of normal saline (GK_Chronic empa, n=11). All rats received control or medicated diet for 4 weeks, and then received an acute i.v. injection of either sildenafil or normal saline 4 minutes prior to the in vivo evaluation of erectile function, respectively. Data are mean±SEM.

Figure 2A:
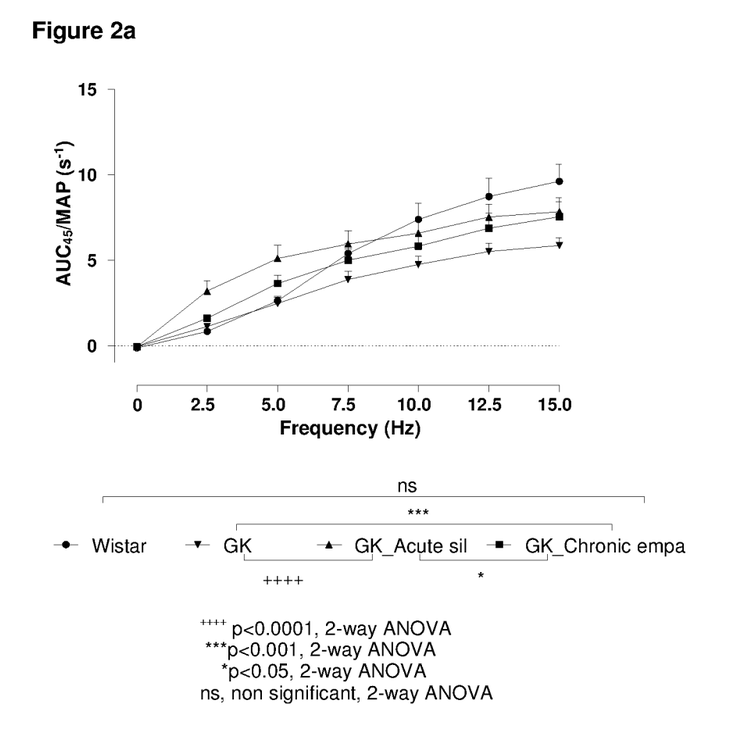
FIGS. 2a and 2b show erectile responses in terms of $AUC_{45}/MAP$ and $AUC_{tot}/MAP$ elicited by cavernous nerve stimulation at increasing stimulation frequencies in anaesthetized Wistar rats.
Figure 2B:
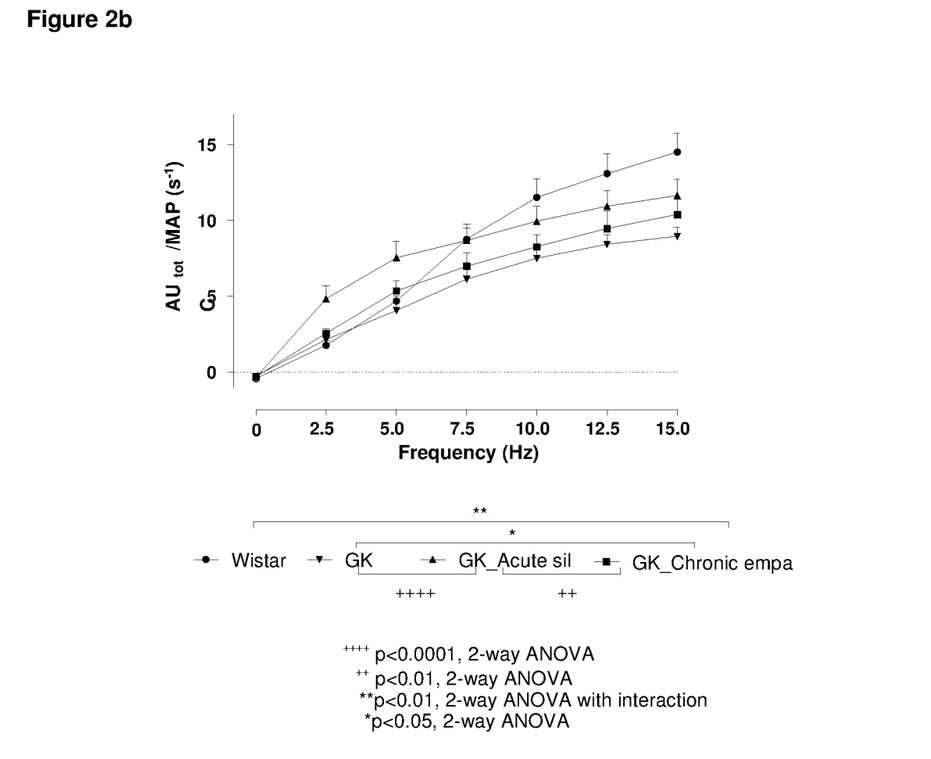

The FIGS. 2a and 2b show erectile responses in terms of $AUC_{45}$/MAP (FIG. 2a) and $AUC_{tot}$/MAP (FIG. 2b) elicited by cavernous nerve stimulation at increasing stimulation frequencies in anaesthetized Wistar rats that received control diet and acute injection of normal saline (WI, n=15), GK rats that received control diet and either acute injection of normal saline (GK, n=10) or sildenafil at 0.3 mg/kg (GK_Acute sil, n=12) and GK rats that received medicated diet i.e., control diet premixed with empagliflozin at 25.3±0.9 mg/kg/day and acute injection of normal saline (GK_Chronic empa, n=11). All rats received control or medicated diet for 4 weeks, and then received an acute IV injection of either sildenafil or normal saline 4 minutes prior to the in vivo evaluation of erectile function, respectively. Data are mean±SEM.

The in vivo erectile responses elicited by electrical stimulation at increasing frequencies of the cavernous nerve characterized by ΔICP/MAP (FIG. 1) as well as both $AUC_{45}$/MAP (FIG. 2a), and $AUC_{tot}$/MAP (FIG. 2b) were significantly reduced in diabetic GK rats compared with age-matched Wistar rats.

Intravenous injection of sildenafil (0.3 mg/kg) significantly increased the erectile response to ES CN in diabetic GK rats in terms of ΔICP/MAP (p<0.0001, 2-way ANOVA, FIG. 1), $AUC_{45}$/MAP (p<0.0001, 2-way ANOVA, FIG. 2a) and $AUC_{tot}$/MAP (p<0.0001, 2-way ANOVA, FIG. 2b).

Figure 3:
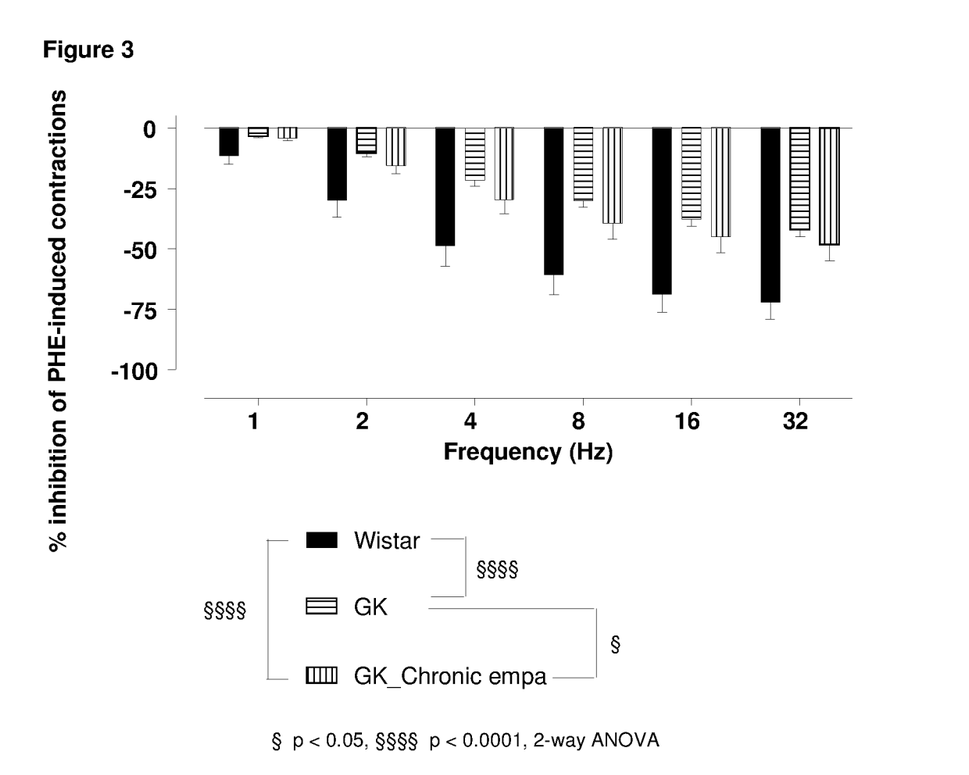

The FIG. 3 shows relaxant responses elicited by increasing frequencies of EFS on PHE-induced contractions of CC strips from Wistar rats and diabetic GK rats that received control diet and diabetic GK rats that received medicated diet i.e., control diet premixed with empagliflozin at 25.3±0.9 mg/kg/d. All rats received control or medicated diet for 4 weeks.

Chronic administration of empagliflozin premixed with diet at an average daily dose of 25.3±0.9 mg/kg/day for 4 weeks improved the erectile responses to ES CN in diabetic GK rats in terms of $AUC_{45}$/MAP (p<0.05, FIG. 2a) and $AUC_{tot}$/MAP (p<0.05, FIG. 2b) compared to those observed in diabetic GK rats that received control diet. When examining the results obtained for ΔICP/MAP, chronic empagliflozin seems to improve erectile responses compared to diabetic GK rats that received control diet, although no difference could be statistically detected (p=0.08, 2-way ANOVA, FIG. 1).

In the following in vitro nitrergic non-adrenergic non-cholinergic neurogenic relaxation responses of isolated corporal strips to EFS (electric field stimulation) are described.

In diabetic GK rats, the relaxation induced by EFS on PHE precontracted cavernosal strips was slightly but significantly improved by a 4-week treatment of empagliflozin at 25.3±0.9 mg/kg/d (p<0.05, 2-way ANOVA, FIG. 3). although the maximal relaxation induced by EFS at 32 Hz was not significantly different between treated and untreated diabetic rats (−42.0±2.9% versus −48.7±6.6%).

In conclusion, the impairment of erectile responses in GK rats and partially improvement with single dose sildenafil (0.3 mg/kg) is consistent with previous studies (ref A). In this model of ED in diabetic GK rats, chronic treatment with empagliflozin at 25.3±0.9 mg/kg/day slightly but consistently improved erectile function, eventhough only the ratios of $AUC_{45}$/MAP and $AUC_{tot}$/MAP showed a statistically significant improvement. This observed pro-erectile facilitator effect of chronic empaglfilozin remained slightly but significantly lower that an acute IV dose of sildenafil at 0.3 mg/kg. Moreover, chronic administration of empagliflozin slightly but significantly improved nitrergic dysfunction in corporal strips of diabetic GK rats Example of Pharmaceutical Composition and Dosage Form The following example of solid pharmaceutical compositions and dosage forms for oral administration serves to illustrate the present invention more fully without restricting it to the contents of the example. Further examples of compositions and dosage forms for oral administration, are described in WO 2010/092126. The term "active substance" denotes empagliflozin according to this invention, especially its crystalline form as described in WO 2006/117359 and WO 2011/039107.

Tablets containing 2.5 mg, 5 mg, 10 mg, 25 mg of active substance

|  | Active substance | | | |
|---|---|---|---|---|
|  | 2.5 mg/ per tablet | 5 mg/ per tablet | 10 mg/ per tablet | 25 mg/ per tablet |
| Wet granulation | | | | |
| active substance | 2.5000 | 5.000 | 10.00 | 25.00 |
| Lactose Monohydrate | 40.6250 | 81.250 | 162.50 | 113.00 |
| Microcrystalline Cellulose | 12.5000 | 25.000 | 50.00 | 40.00 |
| Hydroxypropyl Cellulose | 1.8750 | 3.750 | 7.50 | 6.00 |
| Croscarmellose Sodium | 1.2500 | 2.500 | 5.00 | 4.00 |
| Purified Water | q.s. | q.s. | q.s. | q.s. |
| Dry Adds | | | | |
| Microcrystalline Cellulose | 3.1250 | 6.250 | 12.50 | 10.00 |
| Colloidal silicon dioxide | 0.3125 | 0.625 | 1.25 | 1.00 |
| Magnesium stearate | 0.3125 | 0.625 | 1.25 | 1.00 |

|  | Active substance | | | |
|---|---|---|---|---|
|  | 2.5 mg/ per tablet | 5 mg/ per tablet | 10 mg/ per tablet | 25 mg/ per tablet |
| Total core Film Coating | 62.5000 | 125.000 | 250.00 | 200.00 |
| Film coating system Purified Water | 2.5000 q.s. | 4.000 q.s. | 7.00 q.s. | 6.00 q.s. |
| Total | 65.000 | 129.000 | 257.00 | 206.00 |

Details regarding the manufacture of the tablets, the active pharmaceutical ingredient, the excipients and the film coating system are described in WO 2010/092126, in particular in the Examples 5 and 6, which hereby is incorporated herein in its entirety.

The invention claimed is:

1. A method for relieving erectile dysfunction in a male patient diagnosed with prediabetes, type 1 diabetes mellitus, type 2 diabetes mellitus or metabolic syndrome comprising administering a therapeutically effective amount of empagliflozin to the male patient, and further comprising administering one or more medicaments selected from the group consisting of phosphodiesterase 5 (PDE5) inhibitors and alprostadil in an effective amount to increase erectile responses elicited by cavernous nerve stimulation at increasing stimulation frequencies.

2. The method according to claim 1, wherein the male patient is over the age of 60 years.

3. The method according to claim 1, wherein empagliflozin is administered in an amount of 2.5 to 25 mg.

* * * * *